US009669254B2

(12) United States Patent
Arredondo

(10) Patent No.: US 9,669,254 B2
(45) Date of Patent: Jun. 6, 2017

(54) INTEGRATED EXERCISE MAT SYSTEM

(71) Applicant: Andrew Arredondo, Tustin, CA (US)

(72) Inventor: Andrew Arredondo, Tustin, CA (US)

( * ) Notice: Subject to any disclaimer, the term of this patent is extended or adjusted under 35 U.S.C. 154(b) by 0 days.

(21) Appl. No.: 15/364,310

(22) Filed: Nov. 30, 2016

(65) Prior Publication Data

US 2017/0080279 A1  Mar. 23, 2017

Related U.S. Application Data

(63) Continuation-in-part of application No. 15/060,472, filed on Mar. 3, 2016, now Pat. No. 9,539,463.

(60) Provisional application No. 62/176,923, filed on Mar. 3, 2015.

(51) Int. Cl.
| | | |
|---|---|---|
| A61B 5/22 | (2006.01) | |
| A63B 21/00 | (2006.01) | |
| A63B 24/00 | (2006.01) | |
| A63B 71/06 | (2006.01) | |

(52) U.S. Cl.
CPC ...... *A63B 21/4037* (2015.10); *A63B 24/0062* (2013.01); *A63B 71/0622* (2013.01); *A63B 71/0669* (2013.01); *A63B 2220/30* (2013.01); *A63B 2220/53* (2013.01); *A63B 2220/836* (2013.01); *A63B 2225/50* (2013.01)

(58) Field of Classification Search
CPC ........... A61B 5/22; A63B 71/00; A63B 15/02; A63B 26/00
USPC ............... 73/379.01, 379.04; 482/1, 8, 9, 23
See application file for complete search history.

(56) References Cited

U.S. PATENT DOCUMENTS

| | | | | | |
|---|---|---|---|---|---|
| 4,702,475 | A | * | 10/1987 | Elstein | A63B 69/0053 273/445 |
| 5,897,457 | A | * | 4/1999 | Mackovjak | A63B 5/16 482/1 |
| 6,336,891 | B1 | * | 1/2002 | Fedrigon | A63B 22/02 434/247 |
| 7,722,501 | B2 | * | 5/2010 | Nicolas | A63B 23/0458 482/1 |
| 8,942,428 | B2 | * | 1/2015 | Snook | G06F 3/011 382/103 |
| 2005/0264088 | A1 | * | 12/2005 | Tadin | A47D 3/00 297/488 |
| 2008/0125290 | A1 | * | 5/2008 | Cabados | A63B 6/00 482/23 |
| 2012/0058861 | A1 | * | 3/2012 | Satut | A63B 21/4037 482/8 |
| 2012/0122636 | A1 | * | 5/2012 | Shurtleff | A63B 21/4037 482/142 |
| 2016/0166876 | A1 | * | 6/2016 | Goh | A63B 24/0062 482/9 |

\* cited by examiner

*Primary Examiner* — Jewel V Thompson
(74) *Attorney, Agent, or Firm* — John D. Tran; Rhema Law Group

(57) ABSTRACT

An integrated exercise mat system can include: a user device having a display for displaying an application, providing a metric, and enabling user inputs; an exercise mat coupled to the user device, the exercise mat having a sensor to detect an article on the exercise mat and to obtain a force measurement exerted by the article through a movement, and the exercise mat having a communication module to communicatively connect the exercise mat with a processor and provide the force measurement to the processor; and wherein the processor performs a plurality of calculations based on the force measurement.

20 Claims, 3 Drawing Sheets

INTEGRATED EXERCISE MAT SYSTEM

CROSS-REFERENCE TO RELATED APPLICATIONS

This is a Continuation-in-Part of U.S. patent application Ser. No. 15/060,472 filed Mar. 3, 2016, which claims the benefit of priority to U.S. Provisional Patent Application 62/176,923 filed Mar. 3, 2015 and claims priority benefit to all common subject matter. The content of these applications is incorporated herein by reference in their entirety.

TECHNICAL FIELD

This disclosure relates to exercise equipment, more particularly to smart, durable, and engaging exercise mats.

BACKGROUND

Conventional exercise mats are generally composed of a relatively firm padding enclosed in quilted covering material. The padding is usually thick and the quilted outer covering is thin and of durable wear-resistant material such as canvas or vinyl sheet. Such mats provide a reasonable degree of cushioning between typical hardwood flooring and the user which is sufficient for many exercises.

Exercise mats, however, have largely been confined to raw materials which have failed to provide engaging, smart exercise equipment integrated with the ever increasing market place of exercise electronics.

Solutions have been long sought but prior developments have not taught or suggested any complete solutions, and solutions to these problems have long eluded those skilled in the art. Thus, there remains a considerable need for devices and methods that can provide engaging, smart exercise equipment integrated with the ever increasing market place of exercise electronics.

SUMMARY

An integrated exercise mat system providing engaging, smart exercise equipment integrated with the ever increasing market place of exercise electronics is disclosed. The integrated exercise mat system can include: a user device having a display for displaying an application, providing a metric, and enabling user inputs; an exercise mat coupled to the user device, the exercise mat having a sensor to detect an article on the exercise mat and to obtain a force measurement exerted by the article through a movement, and the exercise mat having a communication module to communicatively connect the exercise mat with a processor and provide the force measurement to the processor; and wherein the processor performs a plurality of calculations based on the force measurement.

Other contemplated embodiments can include objects, features, aspects, and advantages in addition to or in place of those mentioned above. These objects, features, aspects, and advantages of the embodiments will become more apparent from the following detailed description, along with the accompanying drawings.

BRIEF DESCRIPTION OF THE DRAWINGS

The integrated exercise mat system is illustrated in the figures of the accompanying drawings which are meant to be exemplary and not limiting, in which like reference numerals are intended to refer to like components, and in which.

DETAILED DESCRIPTION

Figure 1:
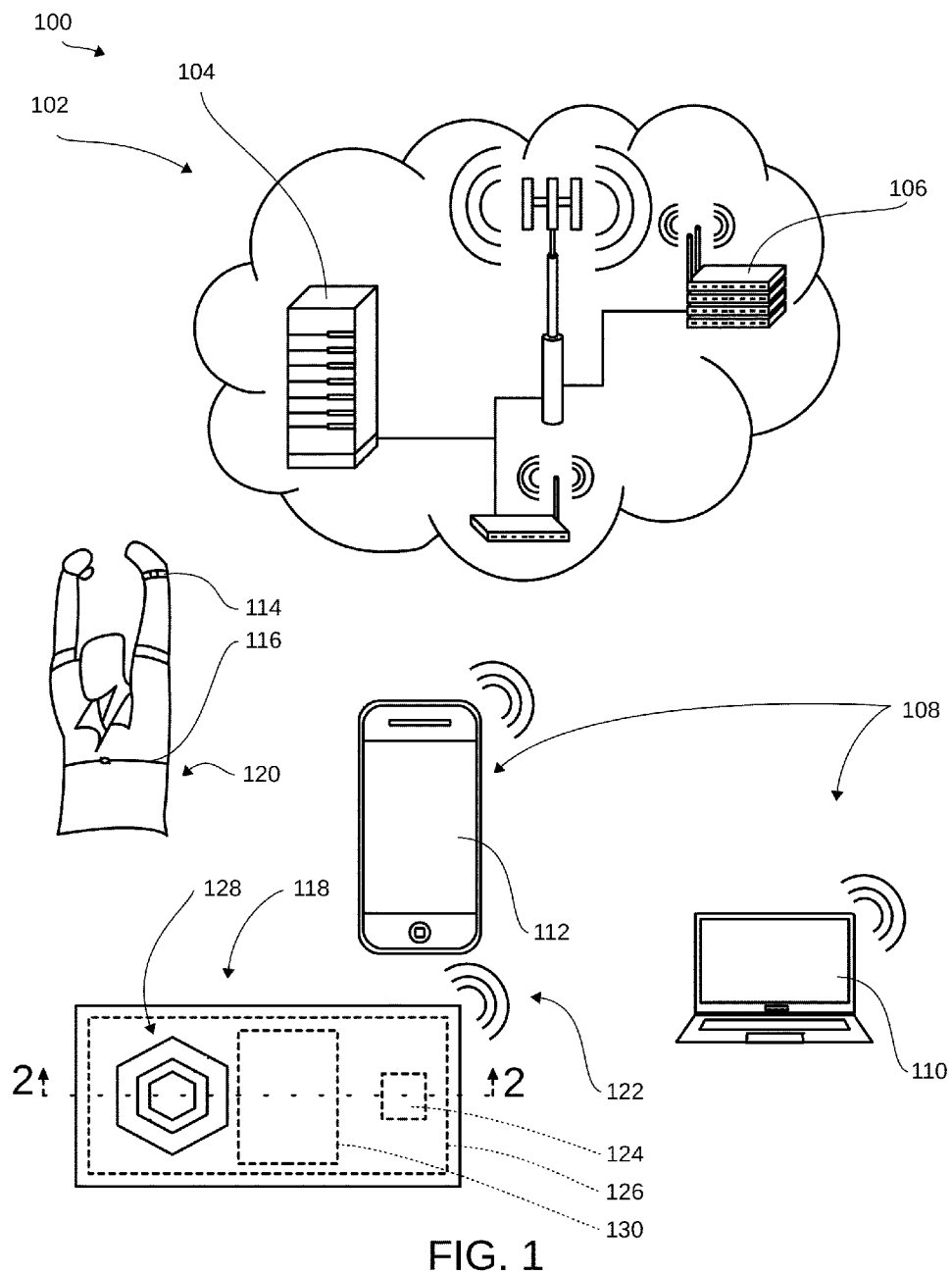
FIG. 1 is a diagram of an integrated exercise mat system.

In the following description, reference is made to the accompanying drawings that form a part hereof, and in which are shown by way of illustration, embodiments in which the integrated exercise mat system may be practiced. It is to be understood that other embodiments may be utilized and structural changes may be made without departing from the scope of the integrated exercise mat system.

When features, aspects, or embodiments of the integrated exercise mat system are described in terms of steps of a process, an operation, a control flow, or a flow chart, it is to be understood that the steps can be combined, performed in a different order, deleted, or include additional steps without departing from the integrated exercise mat system as described herein.

The integrated exercise mat system is described in sufficient detail to enable those skilled in the art to make and use the integrated exercise mat system and provide numerous specific details to give a thorough understanding of the integrated exercise mat system; however, it will be apparent that the integrated exercise mat system may be practiced without these specific details.

To avoid obscuring the integrated exercise mat system, some well-known system configurations are not disclosed in detail. Likewise, the drawings showing embodiments of the system are semi-diagrammatic and not to scale and, particularly, some of the dimensions are for the clarity of presentation and are shown greatly exaggerated in the drawing FIGs. Generally, the integrated exercise mat system can be operated in any orientation.

Various aspects of the present disclosure are directed to an exercise mat. More specifically, and as described in greater detail below, various aspects of the present disclosure are directed to a multi-variable measurement exercise mat that is flexible, portable and contains an internal electrode assembly with multiple sensors embedded within the mat.

Referring now to FIG. 1, therein is shown a diagram of an integrated exercise mat system 100. The integrated exercise mat system 100 can include elements of a distributed computing system 102 including servers 104, routers 106, and another telecommunications infrastructure.

The distributed computing system 102 can include the Internet, a wide area network, (WAN), a metropolitan area network (MAN), a local area network (LAN), a telephone network, cellular data network (e.g., 3G, 4G) and/or a combination of these and other networks (wired, wireless, public, private or otherwise).

The servers 104 can function both to process and store data for use on user devices 108 including laptops 110, cellular phones 112, wearable computers such as watches 114, and wearable sensors 116 such as heart rate monitors, breathing monitors, blood pressure monitors, and blood oxygen content monitors.

It is contemplated that the servers 104 and the user devices 108 can individually comprise a central processing unit, memory, storage and input/output units and other constituent components configured to execute applications including software suitable for displaying user interfaces, the interfaces optionally being generated by a remote server, interfacing with the cloud network, and managing or performing capture, transmission, storage, analysis, display, or other processing of data and or images.

The servers 104 and the user devices 108 of the imaging uniformity system 100 can further include a web browser operative for, by way of example, retrieving web pages or other markup language streams, presenting those pages or streams, executing scripts, controls and other code on those pages or streams, accepting user input with respect to those pages or streams, and issuing HTTP requests with respect to those pages or streams. The web pages or other markup language can be in HAML, CSS, HTML, Ruby on Rails or other conventional forms, including embedded XML, scripts, controls, and so forth as adapted in accord with the teachings hereof. The user devices 108 and the servers 104 can be used individually or in combination to store and process information from the imaging uniformity system 100 in the form of protocol, parameters, images, protocol instructions and protocol guides.

The user devices 108 can be utilized by a user 120. The user devices 108 can be communicatively coupled to an exercise mat 118. The user devices 108 can communicate directly with the exercise mat 118 utilizing a wireless signal 122 or can communicate with the exercise mat 118 through the distributed computing system 102.

The exercise mat 118 is depicted having a computing unit 124. The computing unit 124 can include a processor (e.g., a central processing unit, a microprocessor, a microcontroller, or another suitable programmable device) and a memory unit of non-transitory computer readable medium including instructions for the operation of the exercise mat 118 and the integration and communication of the exercise mat 118 with the user devices 108.

The computing unit 124 can further include a wireless or wired communication module such as a Wi-Fi transceiver, Bluetooth transceiver, infrared transceiver, or LAN transceiver. The computing unit 124 can further include a power supply. The power supply can be a battery with power management circuitry, an outlet 220 or 110 volt supply, or a combination thereof.

In one contemplated embodiment, of the components of the integrated exercise mat system 100 is operatively coupled to a bus. The bus may be any of several types of bus structures including a memory bus or memory controller, a peripheral bus, and a local bus using any of a variety of bus architectures.

The exercise mat 118 is further depicted including a scale 126 for measuring body weight of the user 120 along with the location and distribution of the user's 120 weight on the exercise mat 118. The scale 126 can be formed as a layer within the exercise mat 118 spanning the entire length and width of the exercise mat 118 or, as shown, can span most of the area of the exercise mat 118 while not extending immediately to the edges of the exercise mat 118.

The exercise mat 118 is further depicted including a target 128. The target 128 can provide protection on the exercise mat 118 for various exercises such as the use of a sledgehammer on the mat. For example, it is contemplated that the user 120 may implement a sledgehammer to hit the mat as an exercise. The target 128 can function to decrease the amount of impact and overuse enabling the exercise mat 118 to last longer and provide a higher degree of durability.

It is contemplated that the user devices 108, including the watch 114, the cellular phone 112, the laptop 110, and the wearable sensors 116 can be communicatively coupled with the exercise mat 118. For example, it is contemplated that the exercise mat 118 can incorporate information from the wearable sensors 116 with information from the scale 126 and target 128 to provide a more accurate depiction of the intensity level of the user 120 during an exercise secession.

Further, it is contemplated that information from the scale 126 and the target 128 of the exercise mat 118 can be transferred and displayed on the user devices 108 such as on the watch 114 or the cellular phone 112 for a realtime depiction of the user's 120 exercise performance.

For ease of description, the exercise mat 118 will be described as connected to the cellular phone 112 and the laptop 110 by wireless communication. However, it is contemplated that in other implementations, the exercise mat 118 and the user devices 108 may be connected via a wire.

Yet further, the exercise mat 118 may be connected to a display unit (not shown in FIG. 1). The user 120 of the exercise mat 118 may use the user devices 108 to interact with the exercise mat 118 and to control the exercise mat 118, as described below with regard to FIGS. 3-6.

The exercise mat 118 is shown to be in a rectangular shape. In other contemplated embodiments, the exercise mat 118 may have a different shape and size. For example, the exercise mat 118 may be a square with measurements of 26 inches by 26 inches. In another example, the exercise mat 118 may be a rectangular pad with measurements of 26 inches by 18 inches.

In one contemplated embodiment, the exercise mat 118 is portable and may move with the user 120. In such an implementation, the exercise mat 118 may have a thickness less than 1 inch and may weigh less than 15 pounds. In other examples, the exercise mat 118 may have a permanent location in an environment (e.g., a room in a house). In either example, the exercise mat 118 maintains connection with the computing device. When the exercise mat 118 is powered/turned on, the exercise mat 118 may confirm active connection with the computing device, detect an object or a person on the mat and proceed with measuring weight of the object or the product.

Turning again to the computing unit 124, the computing unit 124 can be implemented as a central processing unit (CPU), a semiconductor-based microprocessor, a graphics processing unit (GPU), a field-programmable gate array (FPGA) to retrieve and execute instructions, other electronic circuitry suitable for the retrieval and execution instructions stored on a non-transitory computer readable medium, or a combination thereof. The non-transitory computer readable medium may be electronic, magnetic, optical, or other physical storage apparatus to contain or store information such as executable instructions, and data. For example, the non-transitory computer readable medium described herein may be a storage drive (e.g., a hard drive), flash memory, Random Access Memory (RAM), any type of storage disc (e.g., a compact disc, a DVD, etc.), and the like, or a combination thereof.

In one implementation, the computing unit 124 may comprise an application that works with the user devices 108. For example, the exercise mat 118 can measure certain data related to the user 120, and the data measured is delivered to the application running on the computing unit 124 of the exercise mat 118, the user devices 108, the distributed computing system 102, or a combination thereof. Further, various calculations may be performed by the application using the data received from the exercise mat 118.

For example, the application may calculate power and energy usage of the user 120 based on the data from the wearable sensors 116 or the sensors within the exercise mat 118 such as the scale 126. The data from the exercise mat 118 and the wearable sensors 116 can be utilized by the application running on the exercise mat 118, the user devices 108, or the distributed computing system 102. In one contemplated implementation, the processor in the computing unit 124 or the user devices 108 may manage the operation of the application and display the end results on a display unit or the user devices 108.

More specifically, the processor in either the user devices 108, the computing unit 124 of the exercise mat 118, or the distributed computing system 102 can receive a command from the user 120 to perform an action related to the exercise mat 118. The user 120 communicates the command by touching the instance window on a display of the user device 108. For example, the user 120 may touch an image of an application shown on the display of the cellular phone 112, the laptop 110, or the watch 114 to launch that application on that device.

The processor communicates the command received from the user 120 to the user device 108, and the user device 108, the computing unit 124 of the exercise mat 118, or the distributed computing system 102 may launch the requested application. An updated instance may be provided to the display unit of the user device 108, and the user device 108 can display an instance of the application, available for the user 120 to operate.

The exercise mat 118 can further include sensors 130 in addition to or in combination with the scale 126. The sensors 130 can measure and/or detect various parameters occurring on or near exercise mat 118 during operation. In one implementation, the sensor measures data related to an object or person on the exercise mat 118.

More specifically, the sensor 130 can read the force of impact on the exercise mat 118. Such force of impact may be by a person (e.g., user 120) using an object or doing a motion (e.g., ball slams, battle ropes, sledgehammer hits, explosive pushups and squats). The sensors 130 measure the amount of force of an individual applied through body weight movement and/or applied force through an object. Additionally, the exercise mat 118 measures speed, strength and endurance of the user 120.

Once this data along with data from the scale 126 and the wearable sensors 116 is transferred to the computing unit 124, the user device 108, or the distributed computing system 102, the application may provide instant feedback for performance assessment for the user 120 by displaying the feedback on the user device 108. It is contemplated that the raw data from the sensors 130, the scale 126, and the wearable sensors 116 can be transformed into a visual depiction of the physical object (such as the user 120 and the placement and forces the user is exerting on the exercise mat 118) and displayed on the user device 108.

In another implementation, the sensors 130 can collect biometric data of the user 120. The sensors 130 may include any suitable biometric sensor configured to measure one or more of but is not limited to, heart rate, pulse rate, temperature, respiration, acceleration, skin resistivity, muscle contractions, and/or alike. In another implementation, more than one sensors may be provided. Each of the sensors 130 may have a different resolution and field of view.

Examples of applications in which the sensors can be used include object detection, object tracking, object recognition, object classification, object segmentation, object capture and reconstruction, optical touch, augmented reality presentation, or other applications. Object detection can refer to detecting presence of an object on the mat. Object tracking can refer to tracking movement of the object.

Object recognition can refer to identifying a particular object, such as identifying a type of the object, identifying a person, and so forth. Object classification can refer to classifying an object into one of multiple classes or categories. Object segmentation can refer to segmenting an object into multiple segments.

Object capture and construction can refer to capturing visual data of an object and constructing a model of the object. Optical touch can refer to recognizing gestures made by a user's hand, a stylus, or other physical artifact that are intended to provide input to a system. The gestures are analogous to gestures corresponding to movement of a mouse device or gestures made on a touch-sensitive display panel. However, optical touch allows the gestures to be made in three-dimensional (3D) space or on a physical target that is not configured to detect user input.

The communication module within the computing unit 124 of the exercise mat 118 can enable the exercise mat 118 to communicate with the user device 108 and the distributed computing system 102. In some examples, the communication module of the computing unit 124 of the exercise mat 118 may include a Wi-Fi® interface, a Bluetooth interface, a 3G interface, a 4G interface, a near filed communication (NFC) interface, and/or any other suitable interface that allows the computing device to communicate via one or more networks. The networks may include any suitable type or configuration of network 120 to allow the exercise mat 118 to communicate with any external systems or devices (e.g., the user device 108 and the distributed computing system 102).

As mentioned earlier, the display may be a standalone unit or a part of the user device 108 or may be a part of the exercise mat 118. In either implementation, the display unit may be a transparent an organic light emitting diode (OLED) display, or any other suitable display.

The display may be a flexible display that can be wrapped and unwrapped with the exercise mat 118. An attachment section of the display facilitates a coupling of flexible display to a bar in any conventional manner.

In one implementation, the flexible display may have a magnetic disclosure, and the display wrapped around the bar may be held in place with the magnetic disclosure. Alternatively, a band may be used to hold the wrapped display around the bar.

In various implementations, the flexible display screen may have a variety of structural configuration and material composition. The display may support high display resolutions of 1920×1080, or any other suitable display resolutions. When the display screen supports a 1920×1080 display resolution, 1920 is the total number of pixels across the height of the display and 1080 is the total number of pixels across the height of the display.

The display is to display content from the application communicated to the exercise mat 118. As discussed above, the display may be connected to the exercise mat 118 (if not in the mat) via VGA, HDMI, USB Wi-Fi, Bluetooth, over the local network or over the internet cloud.

It should be noted that the position of the user 120 using the exercise mat 118 is dependent on the type of movement being performed. If the user 120 is measuring force of impact with a slam ball, the feet of the user 120 are close to the outside of the exercise mat 118, not on the exercise mat 118 and the slamming of the ball onto the exercise mat 118 is measured.

If the user 120 is measuring the force of a push up or squat jump, then hands or feet of the user 120 are respectively on the exercise mat 118. In one implementation, as described in detail above, the exercise mat 118 can be used in the health and fitness industry by personal trainers, physical therapists, athletic coaches, and other companies that sell fitness and performance equipment.

However, it should be noted that in other implementations, the exercise mat 118 may be utilized for many other areas including, education, gaming, healthcare, and alike. Other examples may be provided while still complying with the principles disclosed herein.

Figure 2:
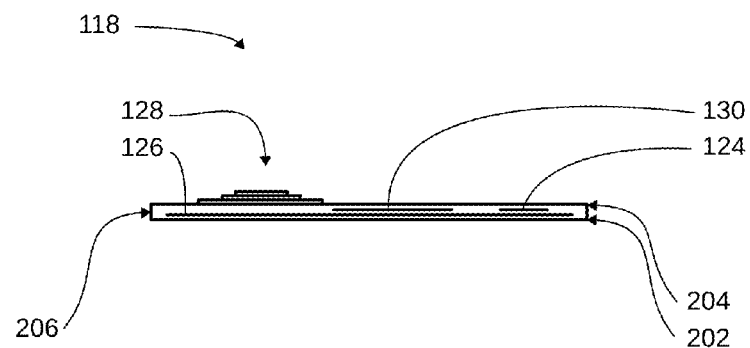
FIG. 2 is a cross-sectional view of the exercise mat of FIG. 1 along the line 2-2 of FIG. 1.

Referring now to FIG. 2, therein is shown a cross-sectional view of the exercise mat of FIG. 1 along the line 2-2 of FIG. 1. The exercise mat 118 is depicted including the target 128, the scale 126, the computing unit 124, and the sensors 130.

As will be appreciated, the exercise mat 118 may have a plurality of layers. More specifically, the exercise mat 118 may have a bottom layer 202. The bottom layer 202 is depicted as downward facing and can be made up of rubber, providing texture to prevent sliding.

In addition, the exercise mat 118 is shown having a top later 204. The top later 204 is upward facing and can be made up of rubber to provide durability.

Further, the exercise mat 118 can include a middle layer 206. The middle layer 206 can include the computing unit 124, the scale 126, and the sensors 130.

The target 128 can be formed with additional layers above the top later 204. The target 128 can serve to protect the layers of the exercise mat 118 as well as the internal components of the exercise mat 118 like the scale 126, the sensors 130, and the computing unit 124.

Figures 3, 4:
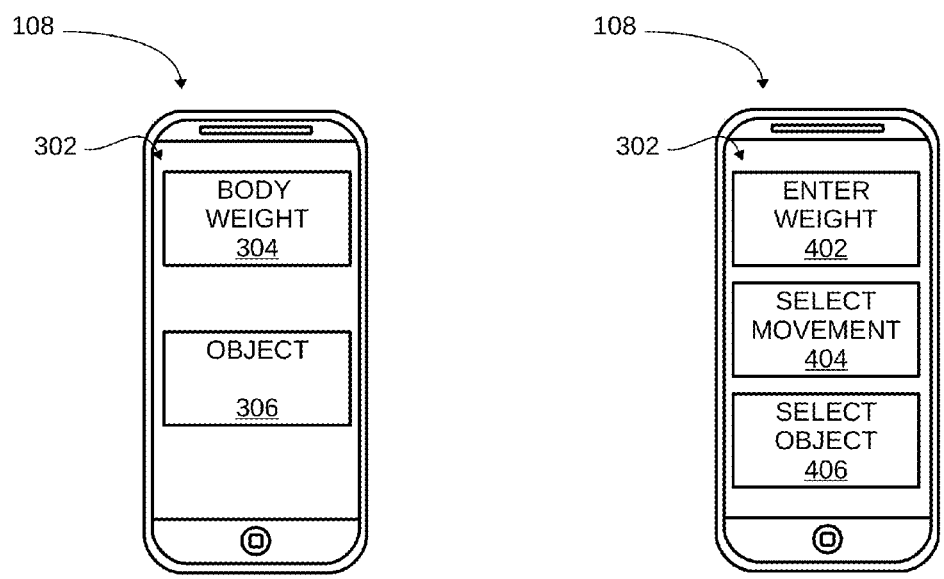
FIG. 3 is a first graphical display of the user device for the integrated exercise mat system of FIG. 1.
FIG. 4 is a second graphical display of the user device for the integrated exercise mat system of FIG. 1.

Referring now to FIG. 3, therein is shown a first graphical display of the user device 108 for the integrated exercise mat system 100 of FIG. 1. The user device 108 is depicted as the cellular phone 112 of FIG. 1; however, it is to be understood that the integrated exercise mat system 100 can be practiced by utilizing any of the user device 108 as described with regard to FIG. 1.

The user device 108 is depicted displaying an application 302 for use with the integrated exercise mat system 100. The application 302 can be displayed, updated, and executed by processors within the computing unit 124 of FIG. 1 of the exercise mat 118 of FIG. 1, the distributed computing system 102 of FIG. 1, or the user devices 108.

The exercise mat 118 can be attached to the user device 108 either using wireless communication or wired communication. In this illustrative example, the application 302 can allow the user 120 of FIG. 1 to provide input to set up the application 302 to work with the exercise mat 118.

The application 302 can provide the user 120 with body weight 304 or object 306 selections. The body weight 304 can be selected if the user 120 is measuring the force of a push up or squat jump. The object 306 can be selected if the user 120 is measuring force of impact with an object 306 such as a slam ball, and the slamming of the ball onto the exercise mat 118 is measured.

Illustratively, the user 120 can either enter the user's 120 body weight 304 or can enter a type of object like a ball slam, or battle ropes by selecting the object 306 option.

Referring now to FIG. 4, therein is shown a second graphical display of the user device 108 for the integrated exercise mat system 100 of FIG. 1. Continuing with the example of the application 302 from FIG. 3, the user 120 of FIG. 1 can be prompted to enter a weight 402, select a movement 404, or select an object 406.

When the user 120 chooses to select a movement 404, the application 302 can prompt the user 120 to enter a movement such as squat jumps, explosive push-ups, or ice skater. When the user 120 selects enter a weight 402, the user 120 can enter their weight. When the user 120 selects select an object 406 the user 120 can select from a list of objects.

Figure 5:
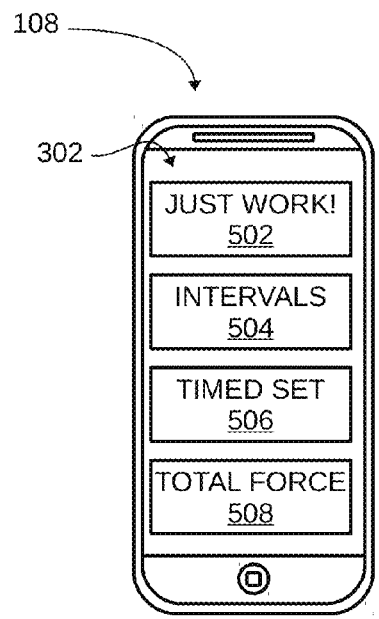
FIG. 5 is a third graphical display of the user device for the integrated exercise mat system of FIG. 1.

Referring now to FIG. 5, therein is shown a third graphical display of the user device 108 for the integrated exercise mat system 100 of FIG. 1. Continuing with the application 302 example from FIGS. 3 and 4, the application 302 can provide selections to the user 120 of FIG. 1 for various settings that may be related to the intensity and duration of the movement or exercise being performed on the exercise mat 118 of FIG. 1.

For example, the user 120 can select a just work 502 selection if the user 120 wishes to begin a work out immediately. The just work 502 selection can begin the monitoring of the user 120 by the exercise mat 118 of FIG. 1 using preset or previously set selections by the user 120.

The user 120 can select intervals 504, timed set 506, or total force 508 to engage the application 302 in different preset workout routines.

Figure 6:
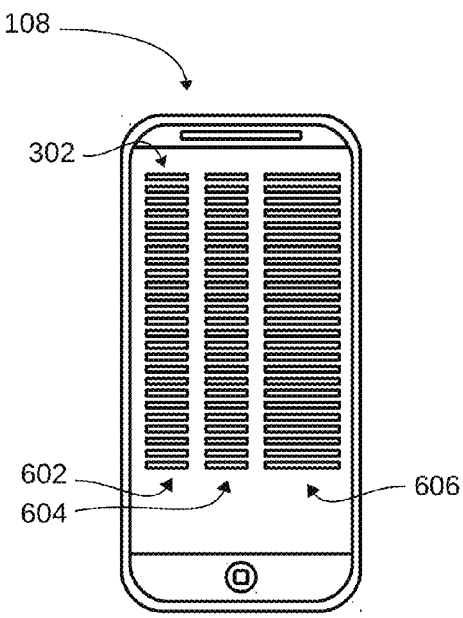
FIG. 6 is a fourth graphical display of the user device for the integrated exercise mat system of FIG. 1.

Referring now to FIG. 6, therein is shown a fourth graphical display of the user device 108 for the integrated exercise mat system 100 of FIG. 1. Continuing with the example application 302 of FIGS. 3-5, the user device 108 can display a leader board having the user 120 listed along with metrics and statistics of their workout performed on the exercise mat 118.

The leader board can provide columns for identifying the various users 120 in a user column 602. The leader board can further provide a column for a time stamp 604. The time stamp 604 can be the date and time that the exercise was performed.

The leader board can further provide a metrics column 606. The metrics column 606 can list a metric or statistic for the exercise performed by the user 120. For example, the metrics column 606 can be a force measurement for an object such as a sledge hammer or weight ball on the exercise mat 118 from the scale 126 or the sensors 130. Further the metrics can include data or statistics from the wearable sensors 116 or the watch 114. The metrics column 606 might further include compiled statistics, for example the total force applied to the exercise mat 118 divided by the body weight of the user 120. Further, the metrics column 606 can additionally include time or intensity metrics collected from the sensors 130, the scale 126, the wearable sensors 116, or the watch 114.

The rows of the leader board can group one of the users 120 with the date of the workout and the statistics pertaining to the workout specified in the row and user 120. It is further contemplated that the leader board can group workouts. For example, the leader board might display all squat workouts together, while not showing sledge hammer workouts based on the user 120 selecting the leader board for squats.

Figure 7:
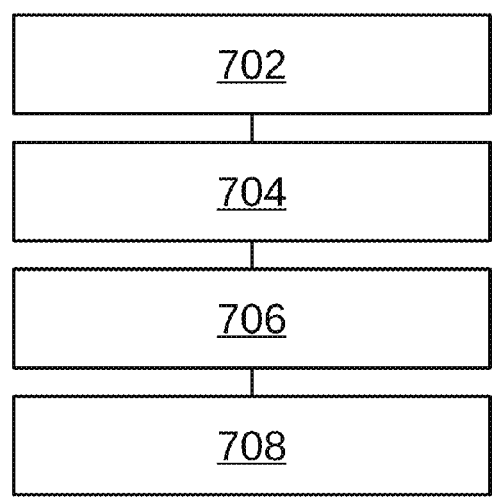
FIG. 7 is a flow chart for the operation of the integrated exercise mat system of FIG. 1.

Referring now to FIG. 7, therein is shown a flow chart for the operation of the integrated exercise mat system of FIG. 1. The flow chart can begin when the integrated exercise mat system 100 of FIG. 1 receives a selection identifying an article in a block 702. The article may be an object or a person as depicted in FIGS. 3-4, as an illustrative example.

The integrated exercise mat system 100 can measure a force in a block 704. It is contemplated that the scale 126 of FIG. 1, the sensors 130 of FIG. 1 of the exercise mat 118 of FIG. 1, the watch 114 of FIG. 1, or the wearable sensors 116 of FIG. 1 can measure the amount of force, heart rate, blood pressure, oxygen saturation, impact location, weight, or acceleration of the user 120. It is contemplated that these measurements could be compiled through the scale 126, the sensors 130, the wearable sensors 116, or the watch 114 during an exercise routine.

The sensors 130 or the scale 126 can measure the amount of force of an individual applied through body weight movement and/or applied force through an object. In one implementation, such force of impact may be by a person (e.g., user 120) using an object or doing a motion (e.g., ball slams, battle ropes, sledgehammer hits, explosive pushups and squats).

The integrated exercise mat system 100 can further execute a transfer and process step in a block 706 where the data collected by the sensors 130, the scale 126, the wearable sensors 116, or the watch 114 can be transferred to a processor. The processor can be within the computing unit 124 of FIG. 1, the user device 108 of FIG. 1, or the distributed computing system 102 of FIG. 1.

Once this data is transferred and stored in non-transitory computer readable medium, the application 302 of FIG. 3 can process and utilize the data from the scale 126, the sensors 130, the wearable sensors 116, or the watch 114. It is contemplated that the application 302 can calculate various metrics such as speed, strength, endurance, and fitness of the user or, when appropriate, the object.

Further, the application 302 provides feedback for performance assessment for the user 120 in a block 708. The application 302 may display the leader board of FIG. 6 or other results and summaries of the workout or the data collected by the exercise mat 118.

Thus, it has been discovered that the integrated exercise mat system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the integrated exercise mat system has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

What is claimed is:

1. An integrated exercise mat system comprising:
a user device having a display for displaying an application, providing a metric, and enabling user inputs;
an exercise mat coupled to the user device, the exercise mat having a sensor to detect an article on the exercise mat and to obtain a force measurement exerted by the article through a movement, and the exercise mat having a communication module to communicatively connect the exercise mat with a processor and provide the force measurement to the processor; and
wherein the processor performs a plurality of calculations based on the force measurement.

2. The system of claim 1 wherein the exercise mat is coupled to the user device wirelessly with the communications module.

3. The system of claim 1 further comprising a target formed on or within a top later of the exercise mat.

4. The system of claim 1 wherein the application displayed on the user device includes a leader board displaying the user, a timestamp, and the metric of an exercise.

5. The system of claim 1 wherein the sensor is a scale.

6. The system of claim 1 wherein the processor performs a plurality of calculations based on data from a wearable sensor.

7. The system of claim 1 wherein the article is the user or an object.

8. A non-transitory computer readable medium, useful in association with a processor, including instructions configured to:
display an application on a display of a user device;
detect user inputs from a user, the user inputs detected within the application;
communicatively couple an exercise mat to the user device with a communication module;
detect an article on the exercise mat with a sensor;
obtain a force measurement with the sensor, the force measurement exerted by the article through a movement;
provide the force measurement to the processor;
perform a plurality of calculations based on the force measurement; and
display a metric within the application on the display of the user device.

9. The computer readable medium of claim 8 wherein the instructions configured to communicatively couple the exercise mat to the user device includes instructions configured to wirelessly couple the exercise mat to the user device with the communications module.

10. The computer readable medium of claim 8 wherein the instructions configured to obtain the force measurement include instructions configured to obtain the force measurement on a target formed on or within a top later of the exercise mat.

11. The computer readable medium of claim 8 wherein the instructions configured to display the metric include instructions configured to display a leader board, the leader board displaying the user, a timestamp, and the metric of an exercise.

12. The computer readable medium of claim 8 wherein the instructions configured to obtain the force measurement include instructions configured to obtain the force measurement with a scale.

13. The computer readable medium of claim 8 further comprising instructions configured to perform a plurality of calculations based on data from a wearable sensor.

14. The computer readable medium of claim 8 wherein the instructions configured to detect the article on the exercise mat include instructions configured to detect a user or an object on the exercise mat.

15. A method of operating an integrated exercise mat system comprising:
displaying an application on a display of a user device;
detecting user inputs from a user, the user inputs detected within the application;

communicatively coupling an exercise mat to the user device with a communication module;

detecting an article on the exercise mat with a sensor;

obtaining a force measurement with the sensor, the force measurement exerted by the article through a movement;

providing the force measurement to the processor;

performing a plurality of calculations based on the force measurement; and displaying a metric within the application on the display of the user device.

16. The method of claim 15 wherein communicatively coupling the exercise mat to the user device includes wirelessly coupling the exercise mat to the user device with the communications module.

17. The method of claim 15 wherein obtaining the force measurement includes obtaining the force measurement on a target formed on or within a top later of the exercise mat.

18. The method of claim 15 wherein the displaying the metric includes instructions configured to display a leader board, the leader board displaying the user, a timestamp, and the metric of an exercise.

19. The method of claim 15 wherein obtaining the force measurement includes obtaining the force measurement with a scale.

20. The method of claim 15 further comprising performing a plurality of calculations based on data from a wearable sensor.

* * * * *